(12) United States Patent
Williams et al.

(10) Patent No.: US 11,944,294 B2
(45) Date of Patent: Apr. 2, 2024

(54) CIRCULAR STAPLING DEVICE WITH ARTICULATING ANVIL RETAINER ASSEMBLY

(71) Applicant: Covidien LP, Mansfield, MA (US)

(72) Inventors: Justin Williams, Southbury, CT (US); Stephen Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/948,592

(22) Filed: Sep. 20, 2022

(65) Prior Publication Data

US 2023/0012329 A1 Jan. 12, 2023

Related U.S. Application Data

(63) Continuation of application No. 15/665,542, filed on Aug. 1, 2017, now Pat. No. 11,452,522.
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07292* (2013.01); *A61B 17/1155* (2013.01);
(Continued)

(58) Field of Classification Search
None
See application file for complete search history.

(56) References Cited

U.S. PATENT DOCUMENTS 3,388,847 A 6/1968 Kasulin et al.
3,552,626 A 1/1971 Astafiev et al.
(Continued)

FOREIGN PATENT DOCUMENTS

CA 908529 A 8/1972
CA 2805365 A1 8/2013
(Continued)

OTHER PUBLICATIONS

European Search Report dated Dec. 12, 2017, issued in European U.S. Appl. No. 17/186,270.
(Continued)

*Primary Examiner* — Tanzim Imam
(74) *Attorney, Agent, or Firm* — Carter, DeLuca & Farrell LLP (57) ABSTRACT

A circular stapling device includes a handle assembly, an elongate body portion that extends distally from the handle assembly, a shell assembly supported on a distal end of the elongate body portion, an anvil retainer assembly extending through the shell assembly, and an anvil assembly supported on the anvil retainer assembly. The anvil retainer assembly includes a retainer member including a retainer body and an engagement member that is pivotally supported on the retainer body. The engagement member is movable axially in relation to the retainer body from a retracted position to an advanced position to move the engagement member to from a locked position to an unlocked position in relation to the retainer body. In the unlocked position, the engagement member is movable from a non-articulated position to an articulated position in relation to the retainer body.

20 Claims, 8 Drawing Sheets

Related U.S. Application Data (60) Provisional application No. 62/375,176, filed on Aug. 15, 2016.

(51) Int. Cl.
 *A61B 17/115* (2006.01)
 *A61B 17/00* (2006.01)

(52) U.S. Cl.
 CPC .............. *A61B 2017/00477* (2013.01); *A61B 2017/07271* (2013.01); *A61B 17/1152* (2013.01)

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A * | 3/1995 | Kuramoto .......... A61B 17/1152 227/19 |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |

(56) References Cited

U.S. PATENT DOCUMENTS

| | | |
|---|---|---|
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |

(56) References Cited

U.S. PATENT DOCUMENTS

| | | | |
|---|---|---|---|
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,662,370 | B2 | 3/2014 | Takei |
| 8,663,258 | B2 | 3/2014 | Bettuchi et al. |
| 8,672,931 | B2 | 3/2014 | Goldboss et al. |
| 8,678,264 | B2 | 3/2014 | Racenet et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,733,611 | B2 | 5/2014 | Milliman |
| 11,452,522 | B2 | 9/2022 | Williams et al. |
| 2003/0111507 | A1 | 6/2003 | Nunez |
| 2004/0073090 | A1 | 4/2004 | Butler et al. |
| 2004/0195289 | A1 | 10/2004 | Aranyi |
| 2005/0023325 | A1 | 2/2005 | Gresham et al. |
| 2005/0051597 | A1 | 3/2005 | Toledano |
| 2005/0107813 | A1 | 5/2005 | Gilete Garcia |
| 2005/0116009 | A1 | 6/2005 | Milliman |
| 2006/0000869 | A1 | 1/2006 | Fontayne |
| 2006/0011698 | A1 | 1/2006 | Okada et al. |
| 2006/0201989 | A1 | 9/2006 | Ojeda |
| 2007/0027473 | A1 | 2/2007 | Vresh et al. |
| 2007/0029363 | A1 | 2/2007 | Popov |
| 2007/0060952 | A1 | 3/2007 | Roby et al. |
| 2007/0075117 | A1 | 4/2007 | Milliman et al. |
| 2009/0173767 | A1 | 7/2009 | Milliman |
| 2009/0230170 | A1* | 9/2009 | Milliman ............ A61B 17/115 227/176.1 |
| 2009/0236392 | A1 | 9/2009 | Cole et al. |
| 2009/0236398 | A1 | 9/2009 | Cole et al. |
| 2009/0236401 | A1 | 9/2009 | Cole et al. |
| 2010/0019016 | A1 | 1/2010 | Edoga et al. |
| 2010/0051668 | A1 | 3/2010 | Milliman et al. |
| 2010/0084453 | A1 | 4/2010 | Hu |
| 2010/0147923 | A1 | 6/2010 | D'Agostino et al. |
| 2010/0163598 | A1 | 7/2010 | Belzer |
| 2010/0224668 | A1 | 9/2010 | Fontayne et al. |
| 2010/0230465 | A1 | 9/2010 | Smith et al. |
| 2010/0258611 | A1 | 10/2010 | Smith et al. |
| 2010/0264195 | A1 | 10/2010 | Bettuchi |
| 2010/0327041 | A1 | 12/2010 | Milliman et al. |
| 2011/0011916 | A1 | 1/2011 | Levine |
| 2011/0114697 | A1 | 5/2011 | Baxter, III et al. |
| 2011/0114700 | A1 | 5/2011 | Baxter, III et al. |
| 2011/0144640 | A1 | 6/2011 | Heinrich et al. |

(56) References Cited

U.S. PATENT DOCUMENTS

| | | |
|---|---|---|
| 2011/0147432 A1 | 6/2011 | Heinrich et al. |
| 2011/0192882 A1 | 8/2011 | Hess et al. |
| 2012/0065665 A1 | 3/2012 | Williams et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1* | 5/2013 | Mozdzierz ......... A61B 17/1155 227/175.1 |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0144969 A1* | 5/2014 | Scheib ............... A61B 17/1155 227/175.1 |
| 2014/0166728 A1* | 6/2014 | Swayze ............. A61B 17/1155 227/176.1 |
| 2014/0299647 A1* | 10/2014 | Scirica ............ A61B 17/07207 227/175.1 |
| 2015/0129636 A1* | 5/2015 | Mulreed ............... A61B 17/115 227/177.1 |
| 2015/0141976 A1* | 5/2015 | Stulen .................. A61B 18/04 606/28 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2016/0374668 A1* | 12/2016 | Measamer ......... A61B 17/1155 227/175.1 |
| 2017/0128068 A1 | 5/2017 | Zhang et al. |
| 2021/0315663 A1* | 10/2021 | Williams ............... A61B 90/70 |

FOREIGN PATENT DOCUMENTS

| | | | |
|---|---|---|---|
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 2873380 A1 | 5/2015 | |
| EP | 2959846 A1 | 12/2015 | |
| EP | 3031408 A1 | 6/2016 | |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| GB | 2509981 A * | 7/2014 | ......... A61B 17/1114 |
| JP | 2004147969 A | 5/2004 | |
| JP | 2013138860 A | 7/2013 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 9835614 A1 | 8/1998 | |
| WO | 0154594 A1 | 8/2001 | |
| WO | 2008107918 A1 | 9/2008 | |

OTHER PUBLICATIONS

Chinese Office Action dated Dec. 24, 2020, issued in corresponding CN Appln. No. 201710697225, 9 pages.

Chinese Office Action dated Sep. 3, 2021, issued in corresponding CN Appln. No. 2017106972250, 7 pages.

* cited by examiner

CIRCULAR STAPLING DEVICE WITH ARTICULATING ANVIL RETAINER ASSEMBLY

CROSS-REFERENCE TO RELATED APPLICATIONS

This application is a continuation of U.S. patent application Ser. No. 15/665,542, filed Aug. 1, 2017, which claims the benefit of and priority to U.S. Provisional Patent Application No. 62/375,176 filed Aug. 15, 2016, the entire disclosures each of which are incorporated by reference herein.

BACKGROUND

1. Technical Description

The present disclosure is directed to a stapling device and, more particularly, to a circular stapling device having an articulating anvil retainer assembly.

2. Background of Related Art

Circular stapling devices for performing circular anastomosis procedures are known. Typically, a circular stapling device includes a handle assembly, an elongate shaft extending distally from the handle assembly, a shell assembly supported on the distal end of the elongate shaft, and an anvil assembly movably supported in relation to the shell assembly. The anvil assembly is releasably supported on a rigid anvil retainer that extends through and is movable in relation to the shell assembly to move the anvil assembly in relation to the shell assembly between spaced and approximated positions.

Circular stapling devices are commonly used to attach two transected body lumen sections together during an anastomosis procedure or to treat tissue on an inner wall of a body lumen during, for example, a hemorrhoidectomy or mucosectomy procedure. During such procedures, the anvil assembly is typically delivered to the surgical site independently of a body of the stapling device and attached to the anvil retainer at the surgical site within the body lumen. Due to the rigidity of the anvil retainer and the confined space within which the stapling device is located, attachment of the anvil assembly to the anvil retainer may be difficult.

Thus, a continuing need exists in the stapling arts for a circular stapling device including structure that facilitates simplified attachment of the anvil assembly to the anvil retainer of the stapling device in confined spaces.

SUMMARY

In one aspect of the present disclosure, a surgical stapling device includes a handle assembly, an elongate body portion extending distally from the handle assembly, a shell assembly supported on a distal end of the elongate body portion and an anvil retainer assembly extending through the shell assembly. The anvil retainer assembly includes a retainer member including a retainer body and an engagement member. The engagement member is pivotally supported on a distal portion of the retainer body and supports an anvil assembly.

In embodiments, the retainer body includes a distal portion having a clevis including spaced fingers and the engagement member includes a proximal extension, wherein the proximal extension of the engagement member is positioned between the spaced fingers of the clevis of the retainer body.

In some embodiments, the proximal extension defines a slot and each of the spaced fingers of the clevis defines a through bore.

In certain embodiments, the surgical stapling device includes a clevis pin positioned through the through bores and the slot to pivotally secure the engagement member to the retainer body.

In embodiments, the slot is elongated to facilitate axial movement of the engagement member in relation to the retainer body between advanced and retracted positions.

In some embodiments, a biasing member is positioned to urge the engagement member towards the retracted position.

In certain embodiments, at least one of the spaced fingers of the clevis includes a tapered end and the proximal portion of the engagement member defines at least one concavity. The tapered end of the at least one finger is positioned to be received in the at least one concavity of the engagement member when the engagement member is in the retracted position to prevent pivotal movement of the engagement member in relation to the retainer body.

In embodiments, the tapered end of the at least one spaced finger and the at least one concavity are positioned and configured such that when the engagement member is moved to the advanced position, the tapered end of the at least one finger is removed from the at least one concavity to allow pivotal movement of the engagement member in relation to the retainer body.

In some embodiments, each of the spaced fingers includes a tapered end and the at least one concavity includes two concavities.

In certain embodiments, the engagement member includes two shoulders, each of the shoulders defining one of the two concavities.

In embodiments, the surgical stapling device includes a housing defining a lumen and the retainer member is movably supported within the lumen of the housing.

In some embodiments, the lumen is dimensioned to move the engagement member from a pivoted position in relation to the retainer body to a non-pivoted position in relation to the retainer body.

In certain embodiments, the anvil retainer assembly includes a threaded drive screw and the retainer member defines a threaded bore. The threaded drive screw is rotatably received within the threaded bore to move the retainer member axially within the housing.

In another aspect of the present disclosure, a method of attaching an anvil assembly of a surgical stapling device to an anvil retainer assembly of the surgical stapling device, in which the anvil retainer assembly includes a retainer member having a retainer body and an engagement member pivotally supported on the retainer body, includes positioning an anvil assembly at a surgical site; positioning the anvil retainer assembly at the surgical site independently of the anvil assembly; pivoting the engagement member to a pivoted position in relation to the retainer member; and securing the anvil assembly to the anvil retainer assembly.

In embodiments, the method further includes retracting the anvil retainer assembly within a lumen of a housing to move the engagement member from the pivoted position to a non-pivoted position in relation to the retainer member.

In embodiments, the method further includes moving the engagement member from a retracted position to an advanced position in relation to the retainer member to unlock pivotal movement of the engagement member.

In embodiments, retracting the anvil retainer assembly within a lumen of a housing includes actuating a drive screw.

BRIEF DESCRIPTION OF THE DRAWINGS

Various embodiments of the presently disclosed circular stapling device including an articulating anvil retainer assembly are described herein with reference to the drawings, wherein.

DETAILED DESCRIPTION OF EMBODIMENTS

The presently disclosed circular stapling device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and any other surgical procedure performed through a small incision or a cannula inserted into a patient's body. Finally, the term "clinician" is used generally to refer to medical personnel including doctors, nurses, and support personnel.

The presently disclosed circular stapling device includes a handle assembly, an elongate body portion that extends distally from the handle assembly, a shell assembly supported on a distal end of the elongate body portion, an anvil retainer assembly extending through the shell assembly, and an anvil assembly supported on the anvil retainer assembly. The anvil retainer assembly includes a retainer member including a retainer body and an engagement member that is pivotally supported on the retainer body. The retainer body has a distal end that is configured to engage a proximal end of the engagement member to retain the engagement member in a locked, non-articulated or non-pivoted position in relation to the retainer body. The engagement member is movable axially in relation to the retainer body from a retracted position to an advanced position to move the engagement member to an unlocked position. In the unlocked position, the engagement member is movable from the non-articulated position to an articulated position in relation to the retainer body. The engagement member can be pivoted during attachment of the anvil assembly to the body of the stapling device in confined locations where the stapling device is not easily manipulated to simplify attachment of the anvil assembly to the anvil retainer assembly.

Figure 1:
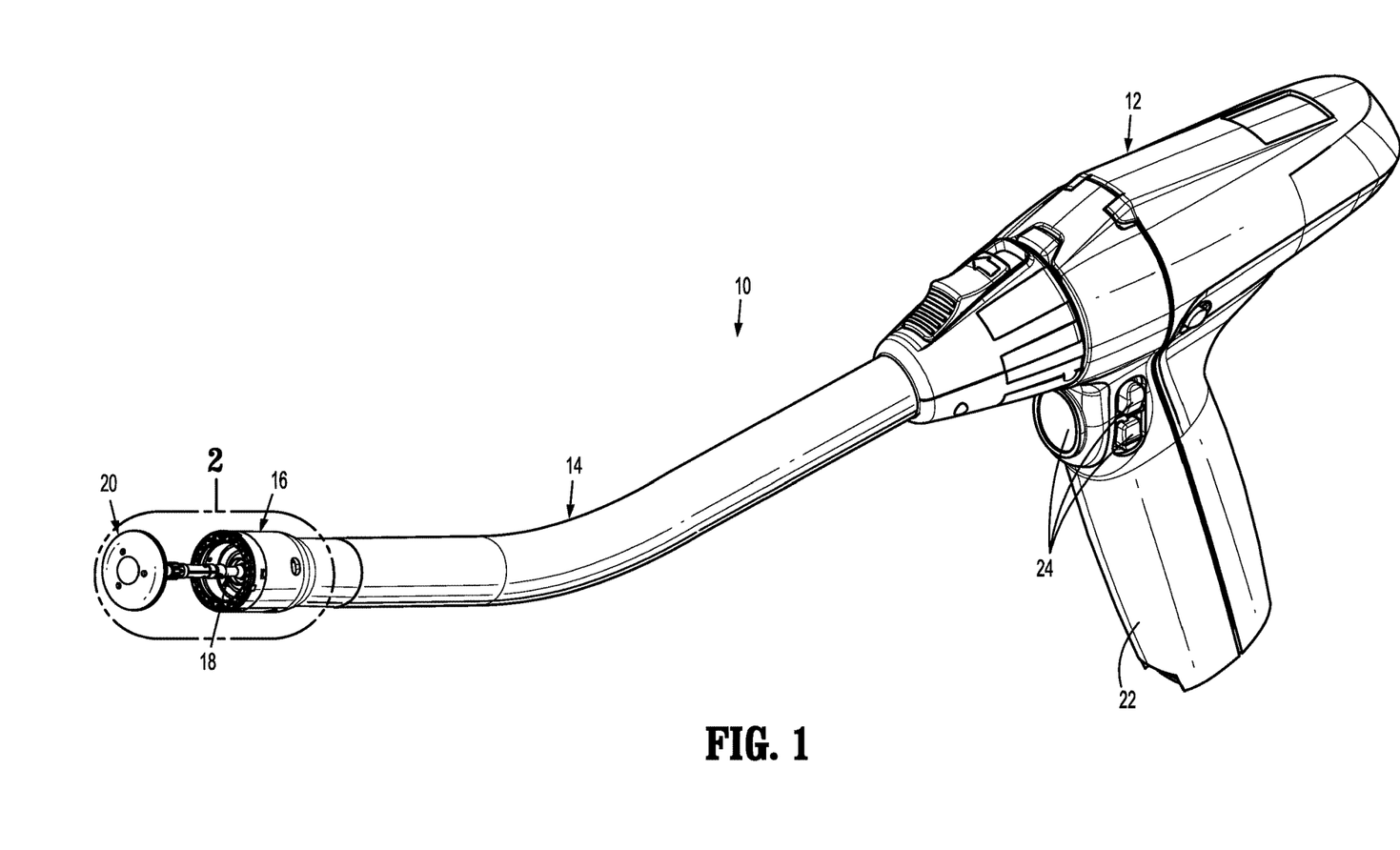
FIG. 1 is a side, perspective view of an exemplary embodiment of the presently disclosed circular stapling device.
Figure 2:
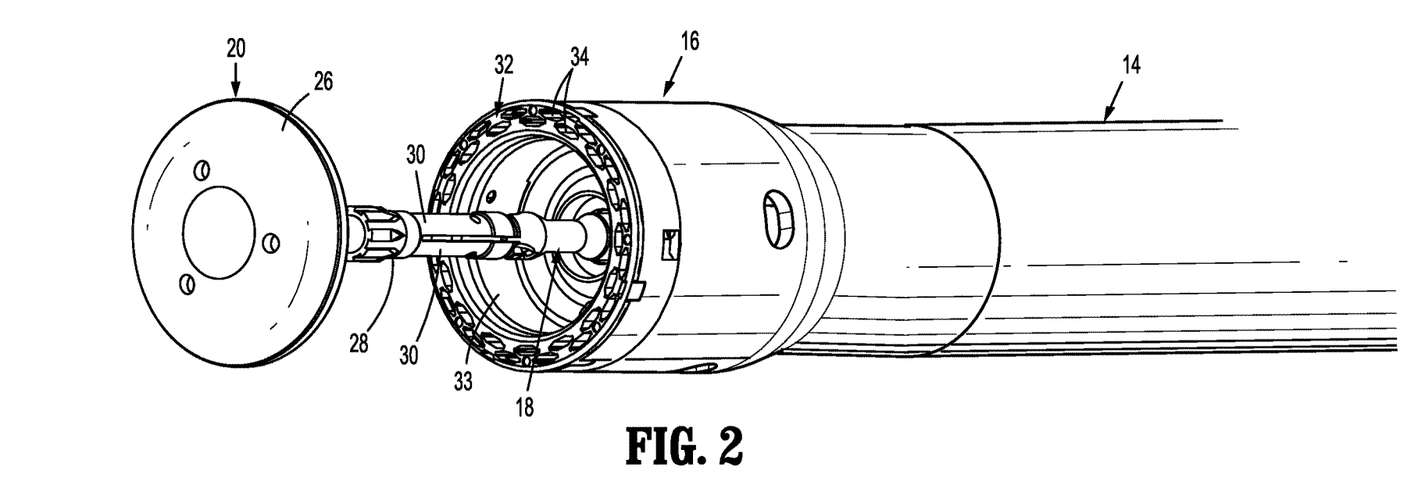
FIG. 2 is an enlarged view of the indicated area of detail shown in FIG. 1.
Figure 3:
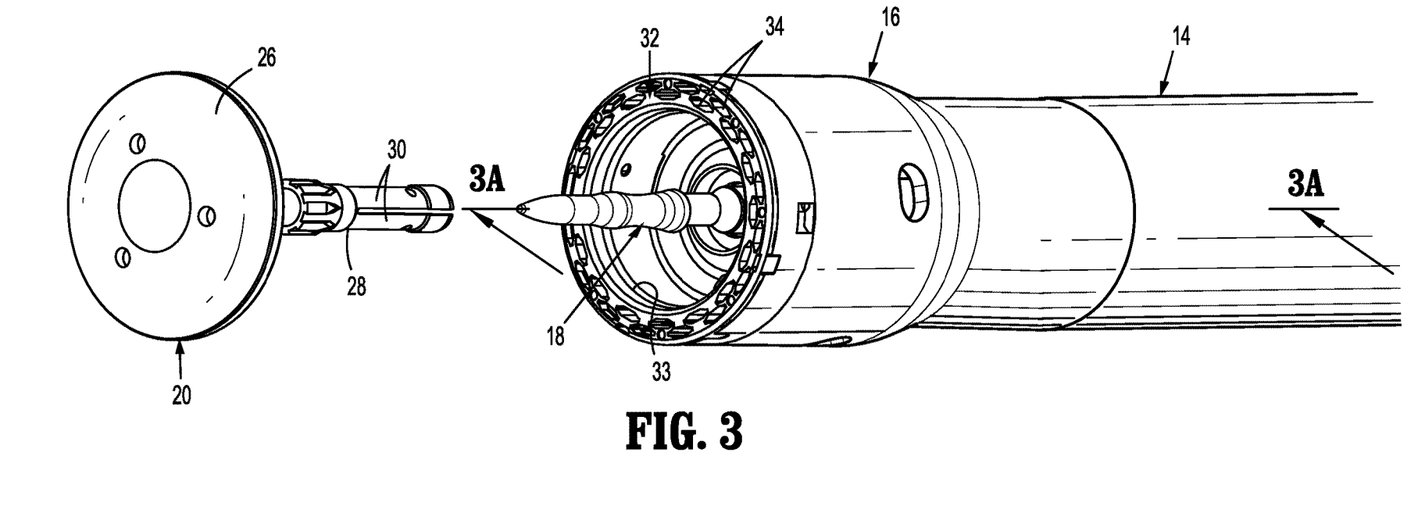
FIG. 3 is a side, perspective view of the distal end of the circular stapling device shown in FIG. 1 with the anvil assembly separated from the anvil retainer assembly.

FIGS. 1-3 illustrate a surgical stapling device 10 including a handle assembly 12, an elongate body 14, a shell assembly 16, an anvil retainer assembly 18, and anvil assembly 20 supported on the anvil retainer assembly 18. The handle assembly 12 is illustrated as a powered assembly and includes a stationary grip 22, and actuation buttons 24 for controlling operation of the stapler functions including approximation of the shell and anvil assemblies 16, 20, and firing of staples (not shown) from the shell assembly 16. The elongate body 14 is illustrated as an adapter assembly that is coupled to the handle assembly 12 to translate power from the handle assembly to the shell and anvil assemblies 16, 20. Although the present disclosure illustrates a powered assembly, it is envisioned that the advantages of the present disclosure as described in detail below are also applicable to surgical stapling devices having manually operated handle and body assemblies. U.S. Pat. No. 7,303,106 ("the '106 patent") discloses an example of a surgical stapling device including a manually actuated handle assembly and is incorporated herein by reference in its entirety. U.S. Pat. No. 9,023,014 ("the '014 patent") and U.S. Pat. No. 9,055,943 ("the '943 patent") disclose examples of surgical stapling devices including exemplary powered handle assemblies. Each of these patents is incorporated herein by reference in its entirety.

Referring to FIGS. 2 and 3, the anvil assembly 20 includes an anvil head 26 and an anvil shaft 28. In the illustrated embodiment, the anvil shaft 28 includes a plurality of resilient fingers 30 that define a bore (not shown) that is configured to receive and releasably engage the anvil retainer assembly 18 as described in further detail below. In embodiments, the anvil head 26 is pivotally coupled to the anvil shaft 28 and is movable between an operative position (FIG. 1) for forming staples and a tilted, reduced profile position (not shown). For a more detailed description of an anvil assembly including an anvil shaft having resilient fingers and a pivotal anvil head, see the '106 patent.

The shell assembly 16 is supported on the distal end of the elongate body 14 and includes an annular cartridge 32 that defines annular rows of staple receiving pockets 34. Each of the staple receiving pockets 34 supports a staple (not shown) that can be fired from the cartridge 32 via actuation of the handle assembly 12 and deformed against the anvil head 26. The shell assembly 18 also includes a pusher (not shown) and an annular knife 33 that are provided to simultaneously eject the staples and dissect tissue, respectively. For a more detailed description of shell assemblies suitable for use with the surgical stapling device 10, see the '106, '014 and '943 patents.

Figure 3A:
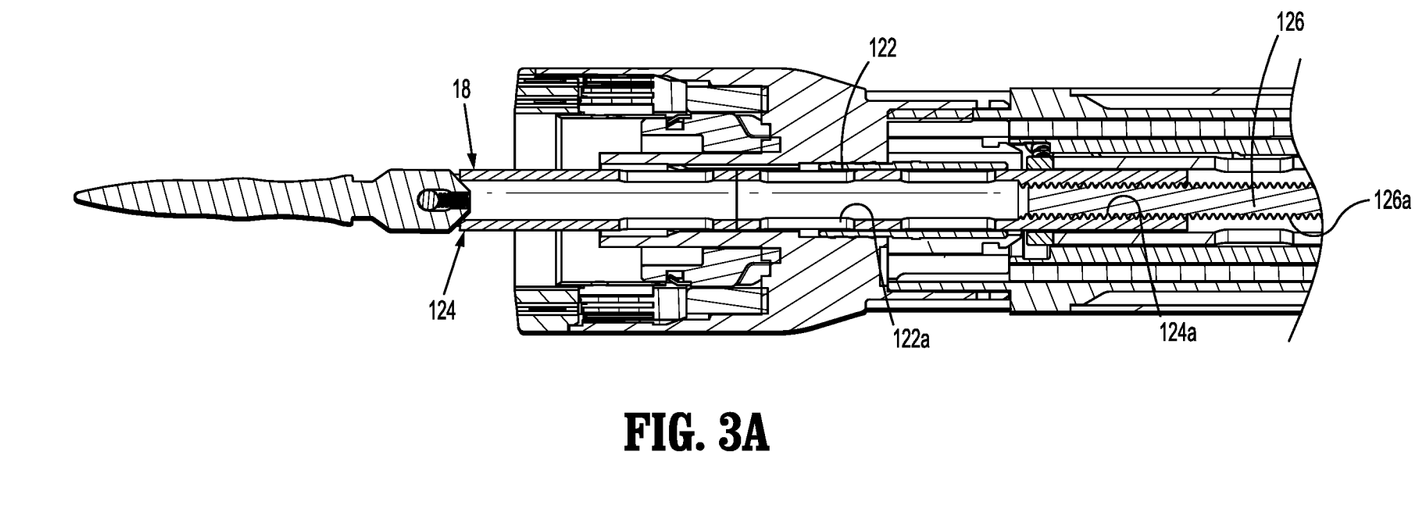
FIG. 3A is a cross-sectional view taken along section line 3A-3A of FIG. 3.
Figures 4, 5:
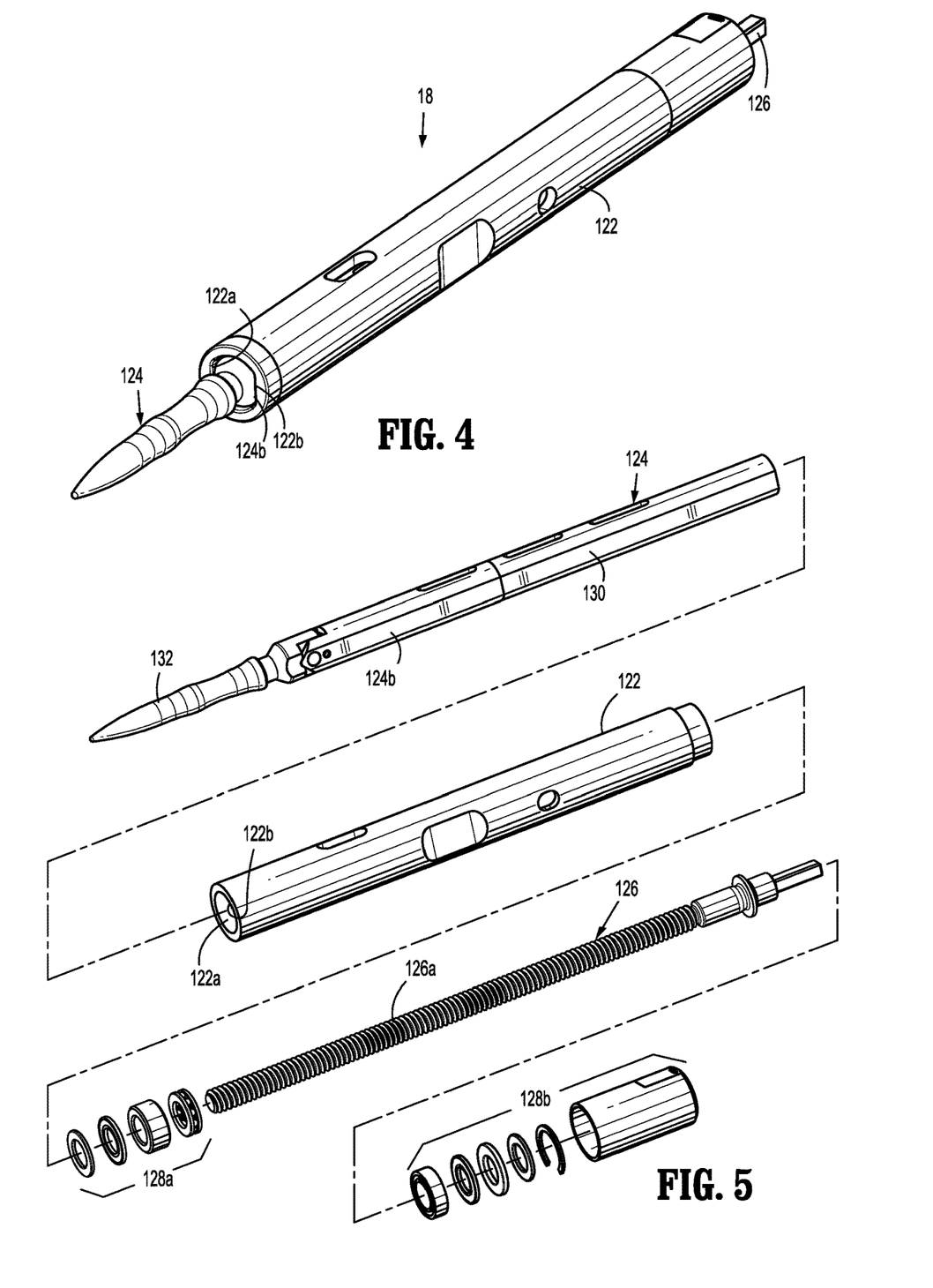
FIG. 4 is a side perspective view of the anvil retainer assembly of the circular stapling device shown in FIG. 1.
FIG. 5 is a side, perspective, exploded view of the anvil retainer assembly shown in FIG. 4.

Referring to FIGS. 3A-5, the anvil retainer assembly 18 of the surgical stapling device 10 includes an outer housing 122 defining a lumen 122a, a retainer member 124 defining a threaded bore 124a (FIG. 3A) movably disposed within the lumen 122a of the outer housing 122, and a drive screw 126 received within the threaded bore 124a of the retainer member 124. The drive screw 126 includes external threads 126a that mate with internal threads formed along the threaded bore 124a (FIG. 3A). When the drive screw 126 is rotated in response to actuation of the handle assembly 12 of the surgical stapling device 10, engagement between the drive screw 126 and the retainer member 124 effects axial movement of the retainer member 124 relative to the outer housing 122. The retainer member 124 includes a longitudinally extending flat 124b. The flat 124b engages a longitudinally extending flat 122b that defines the lumen 122a to prevent rotation of the retainer member 124 within the lumen 122a. A distal portion of the retainer member 124 is configured to releasably engage the anvil assembly 20 (FIG. 1) as described in further detail below. The anvil retainer assembly 18 also includes distal and proximal bearing assemblies 128a, 128b positioned to rotatably support the drive screw 126 in relation to the outer housing 122 of anvil retainer assembly 18. Although the retainer member 124 is illustrated and described to be driven by a rotatable drive screw, it is envisioned that the retainer member 124 may be secured to a manually driven band such as described in the '106 patent.

Figure 6:
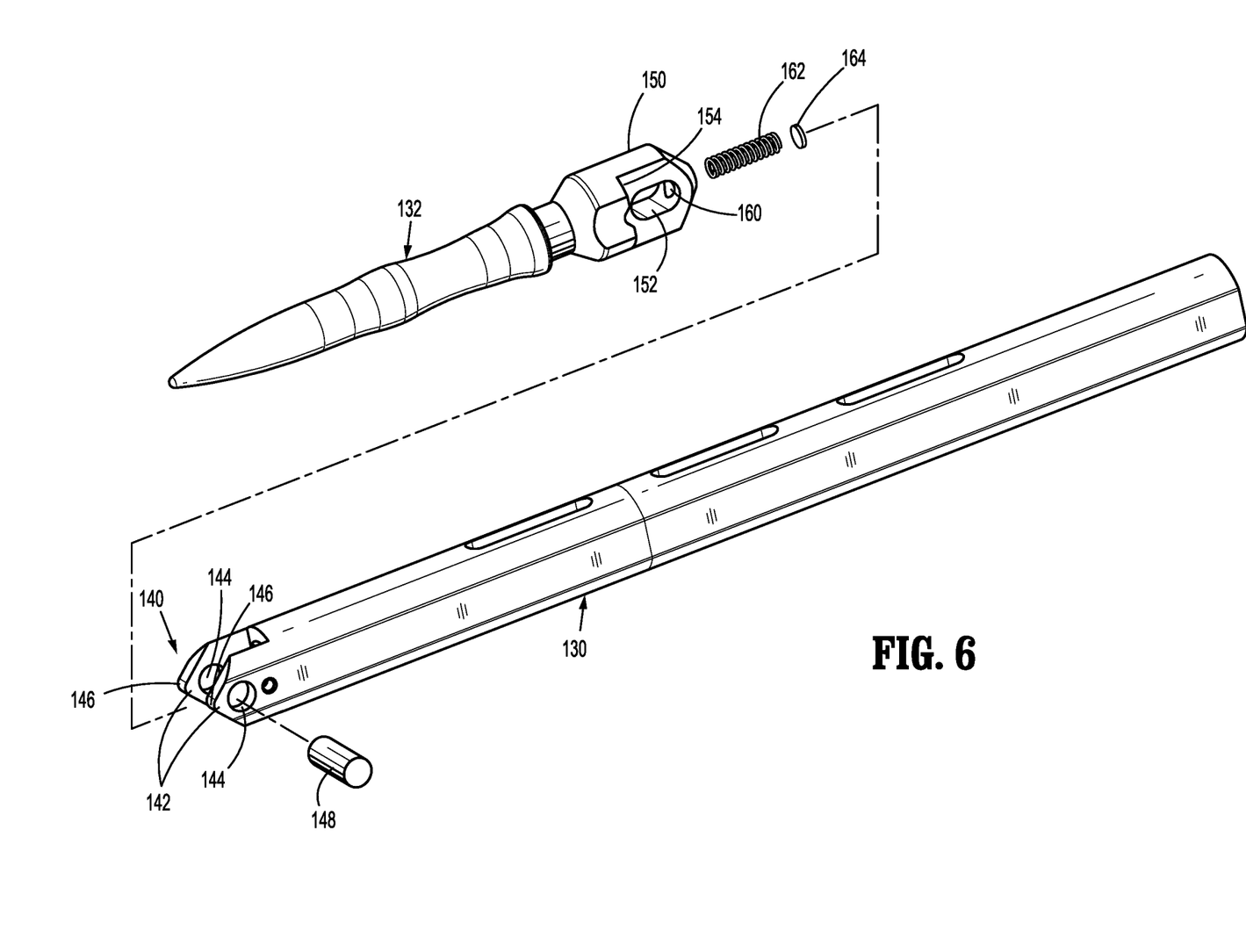
FIG. 6 is an exploded view of the retainer member shown in FIG. 5.
Figure 7:
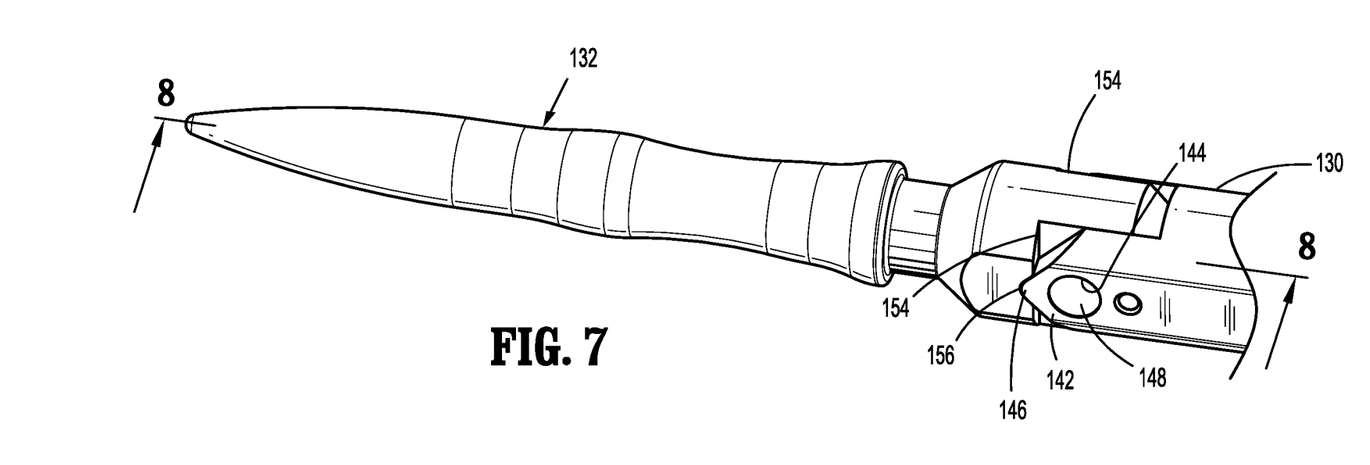
FIG. 7 is a side perspective view of the distal end of the retainer member shown in FIG. 6 in a non-articulated, locked position.
Figure 8:
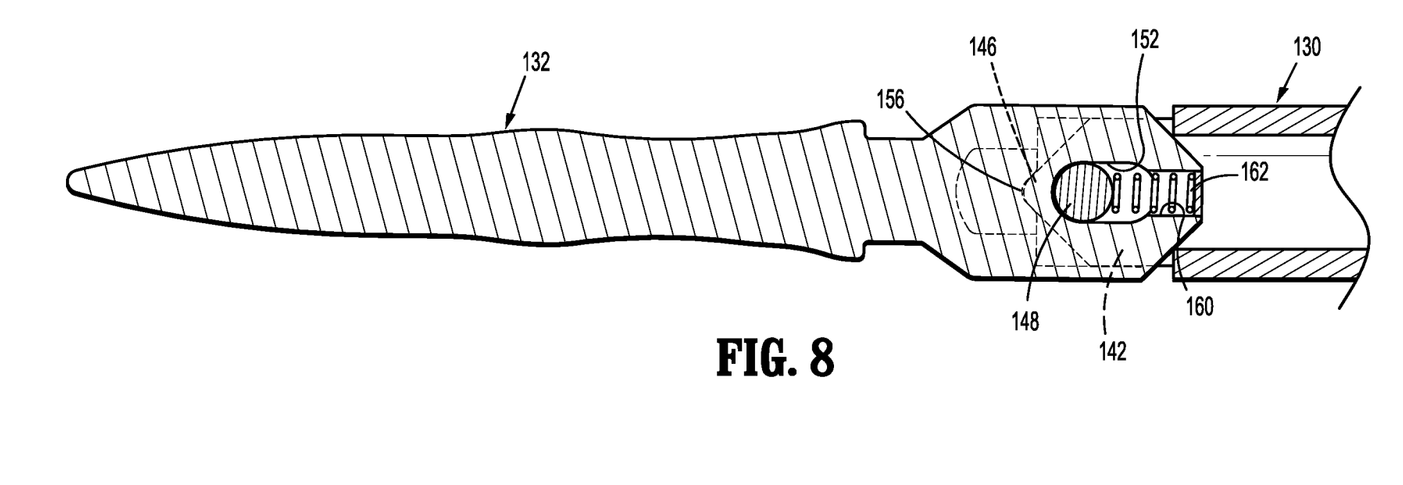
FIG. 8 is a cross-sectional view taken along section line 8-8 of FIG. 7.
Figure 9:
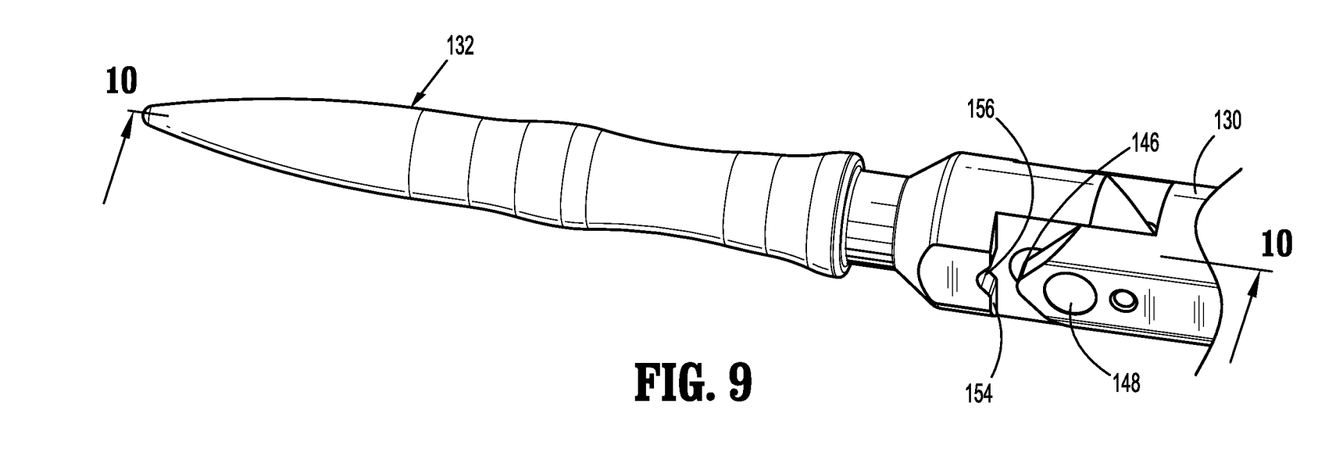
FIG. 9 is a side, perspective view of the distal end of the retainer member shown in FIG. 6 in the non-articulated, unlocked position.

Referring to FIG. 6, the retainer member 124 includes a retainer body 130 and an engagement member 132 that is pivotally secured to a distal portion of the retainer body 130. The distal portion of the retainer body 130 includes a clevis 140 including a pair of spaced fingers 142. Each of the fingers 142 defines a through bore 144 and defines a tapered distal end 146. The through bores 144 are dimensioned to receive a clevis pin 148 as described in detail below. The proximal portion of the engagement member 132 includes a proximal extension 150 that defines an elongated slot 152 and a pair of shoulders 154 (FIG. 7). The proximal extension 150 is configured to be received between the fingers 142 of the clevis 140 such that the through bores 144 are aligned with the elongated slot 152. The clevis pin 148 is positioned through the through bores 144 and the elongated slot 152 to pivotally secure the engagement member 132 to the distal end of the retainer body 130. The through bores 144 are sized to receive the clevis pin 148 in tight, friction fit fashion. The length of the elongated slot 152 of the retainer member 132 is greater than the diameter of the clevis pin 148 such that the engagement member 132 is axially movable in relation to the retainer body 130 from a retracted position (FIG. 7) to an advanced position (FIG. 9).

Referring also to FIGS. 7-10, each shoulder 154 on the proximal end of the engagement member 132 defines a concavity 156 that is dimensioned and configured to receive the tapered distal end 146 of a respective one of the fingers 142 of the clevis 140. When the engagement member 132 is in the retracted position (FIG. 7), the tapered distal end 146 of the fingers 142 are received in the concavities 156 to prevent pivotal movement, i.e., articulation, of the engagement member 132 in relation to the retainer body 130. When the engagement member 132 is in the advanced position (FIG. 9), the tapered distal end 146 of the fingers 142 are spaced from the concavities 156 to allow articulation of the engagement member 132 in relation to the retainer body 130.

The engagement member 132 defines a longitudinal bore 160 (FIG. 8) that extends through the proximal end of the engagement member 132 into communication with the elongated slot 152. The longitudinal bore 160 is dimensioned and configured to accommodate a biasing member 162. An end cap 164 encloses the proximal end of the longitudinal bore 160. In embodiments, the end cap 164 is secured within the longitudinal bore 160 with screw threads (not shown). Alternately, the end cap 164 is secured within the longitudinal bore 160 using any known fastening technique such as welding. The biasing member 162 is positioned between the end cap 164 and the clevis pin 148 to urge the engagement member 132 to the retracted position as shown in FIG. 7. In the retracted position, the clevis pin 148 is positioned in the distal end of the elongated slot 152 of the engagement member 132. When the engagement member 132 is pulled distally in relation to the retainer body 130, the biasing member 162 is compressed between the end cap 164 and the clevis pin 148 (FIG. 10) and the engagement member 132 moves to the advanced position in relation to the retainer body.

Figure 11:
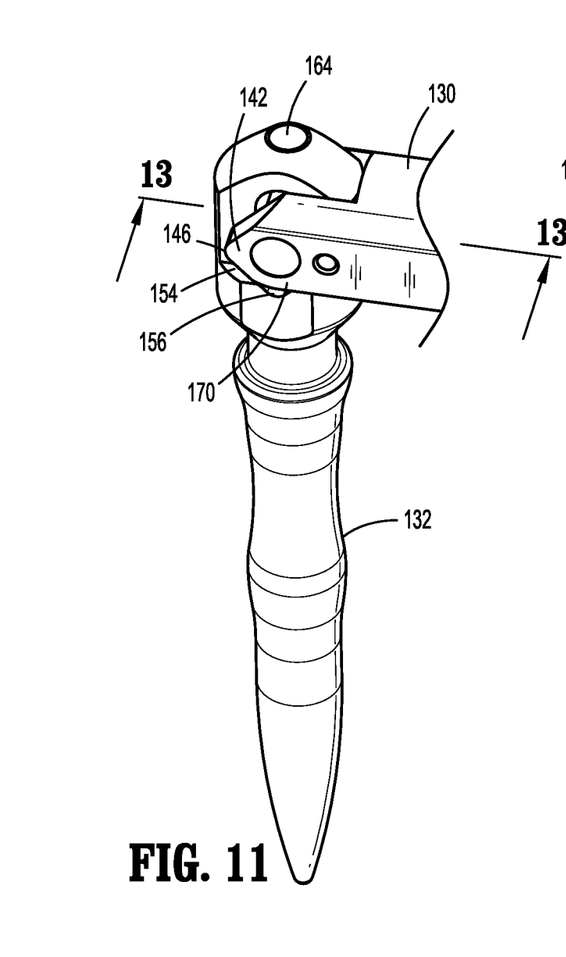
FIG. 11 is a side perspective view from the proximal end of the distal end of the retainer member shown in FIG. 6 in an articulated, unlocked position.
Figure 12:
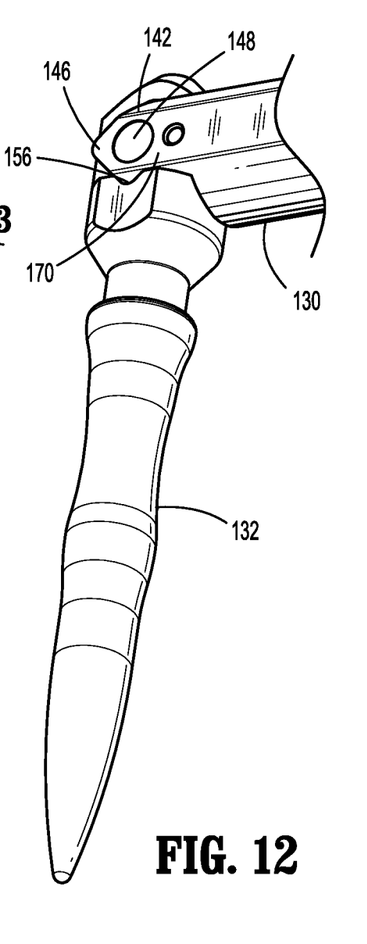
FIG. 12 is a side perspective view from the distal end of the distal end of the retainer member shown in FIG. 6 in an articulated, unlocked position.
Figure 13:
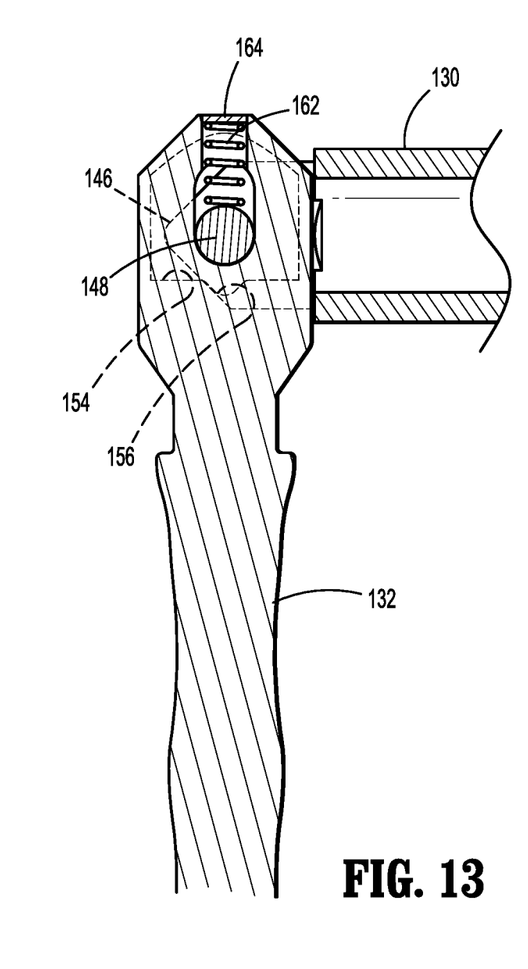
FIG. 13 is a cross-sectional view taken along section line 13-13 of FIG. 11.

Referring to also to FIGS. 11-13, when the engagement member 132 is in the advanced position, the engagement can be articulated about the clevis pin 148 from a position in which the longitudinal axis of the engagement member 132 is aligned with the longitudinal axis of the retainer body 130 (FIG. 7) to a position in which the longitudinal axis of the engagement member 132 is misaligned with the longitudinal axis of the retainer body 130. In embodiments, the shoulders 154 are configured and positioned to engage distal end 170 of the retainer body 130 to limit pivotal movement of the engagement member 132 to define an angle between the longitudinal axis of the engagement member 132 and the longitudinal axis of the retainer body 130 to about ninety degrees. Alternately, the shoulders 154 may be positioned to engage the distal end of the retainer body 130 to limit pivotal movement of the engagement member 132 in relation to the retainer body 130 to other degrees of articulation, e.g., less than thirty degrees.

In embodiments, the engagement member 132 is configured as a trocar having a tapered tip configured to pierce tissue or a suture line and the anvil shaft 28 (FIG. 3) is configured to define a bore (not shown) dimensioned to receive the engagement member 132 to releasably couple the anvil assembly 20 to the anvil retainer assembly 18. It is envisioned that the anvil shaft may be configured as a trocar and the anvil retainer may define a bore configured to receive and releasably couple the anvil assembly to the anvil retainer. For a more detailed description of the engagement member 132 and the coupling engagement between the anvil assembly and the anvil retainer, see the '106 patent.

Figure 10:
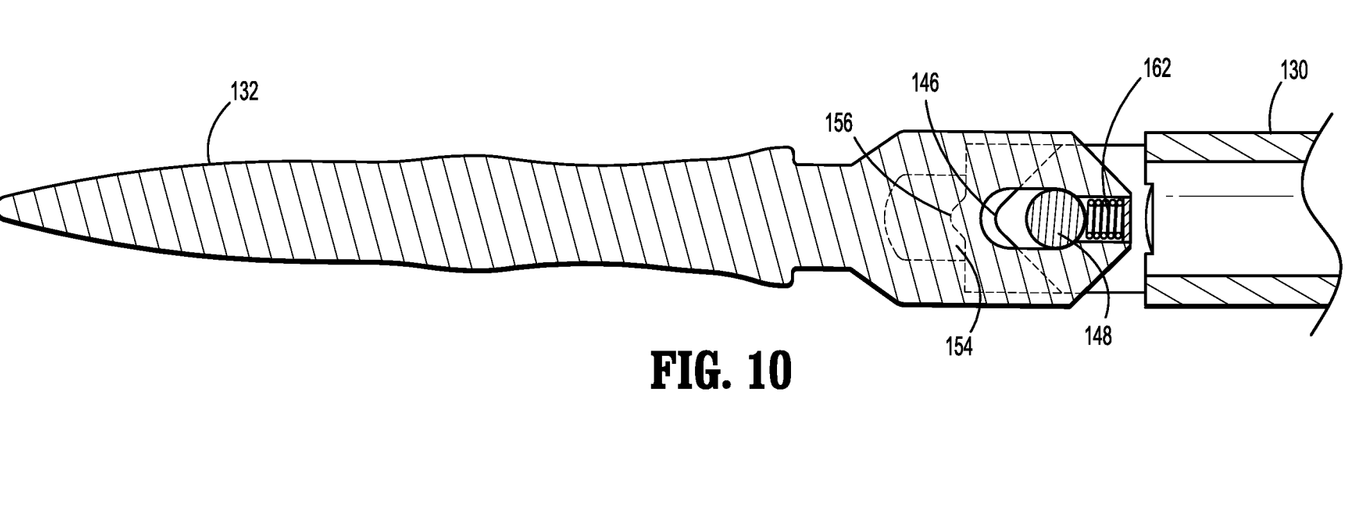
FIG. 10 is a cross-sectional view taken along section line 10-10 of FIG. 9.

When the anvil assembly 20 and the elongate body 14 of the surgical stapling device 10 are positioned at a surgical site (not shown) such that alignment of the anvil shaft 28 of the anvil assembly 20 with the retainer member 124 of the anvil retainer assembly 18 is difficult to effect because of the confined space defining the surgical site, the engagement member 132 of the retainer member 124 can be grasped by a clinician using, e.g., a grasper or other surgical instrument, to move the engagement member 132 from the retracted position (FIG. 8) to the advanced position (FIG. 10). As discussed above, when the engagement member 132 is moved from the retracted position to the advanced position, the concavities 156 formed in the shoulders 154 of the engagement member 132 are moved distally in relation to the tapered distal ends 146 of the fingers 142 to remove the tapered distal ends 146 of the fingers 142 from the concavities 156 to unlock pivotal movement of the engagement 132 in relation to the retainer member 130 to facilitate articulation.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
a handle assembly;
an elongate body portion extending distally from the handle assembly in a distal direction;
a shell assembly supported on a distal end of the elongate body portion, the shell assembly including an annular cartridge positioned on a distal end of the shell assembly;
an anvil retainer assembly extending through the shell assembly, the anvil retainer assembly including a retainer member having a retainer body and an engagement member, the retainer body defining a first longitudinal axis that extends in the distal direction through the annular cartridge and having a distal portion, the engagement member defining a second longitudinal axis and being pivotally supported on the distal portion of the retainer body for movement between a pivoted position in which the first and second longitudinal axes are misaligned and a non-pivoted position in which the first and second axes are coaxial, the engagement member extending distally of the shell assembly and being configured as a trocar having a tapered distal portion for piercing tissue; and
an anvil assembly having an anvil head and an anvil shaft coupled to the anvil head, the anvil shaft releasably coupled to the engagement member of the anvil retainer assembly.

2. The surgical stapling device of claim 1, wherein the distal portion of the retainer body of the anvil retainer assembly includes a clevis and the engagement member includes a proximal extension, the clevis including spaced fingers, the proximal extension of the engagement member positioned between the spaced fingers of the clevis of the retainer body.

3. The surgical stapling device of claim 2, wherein the anvil retainer assembly includes a clevis pin, the proximal extension of the engagement member defining a slot and each of the spaced fingers of the clevis defining a through bore, the clevis pin positioned through the through bores and the slot to pivotally secure the engagement member to the retainer body.

4. The surgical stapling device of claim 3, wherein the slot is elongated, and the clevis pin is axially movable within the slot to facilitate axial movement of the engagement member in relation to the retainer body between advanced and retracted positions.

5. The surgical stapling device of claim 4, further including a biasing member positioned to urge the engagement member towards the retracted position.

6. The surgical stapling device of claim 5, wherein at least one of the spaced fingers of the clevis includes a tapered end and the proximal extension of the engagement member defines at least one concavity, the tapered end of the at least one of the spaced fingers received in the at least one concavity of the engagement member when the engagement member is in the retracted position to prevent pivotal movement of the engagement member in relation to the retainer body.

7. The surgical stapling device of claim 6, wherein the tapered end of the at least one of the spaced fingers and the at least one concavity are positioned and configured such that when the engagement member is moved to the advanced position, the tapered end of the at least one of the spaced fingers is removed from the at least one concavity to allow pivotal movement of the engagement member in relation to the retainer body.

8. The surgical stapling device of claim 7, wherein each of the spaced fingers includes a tapered end and the at least one concavity includes two concavities.

9. The surgical stapling device of claim 8, wherein the engagement member includes two shoulders, each of the shoulders defining one of the two concavities.

10. The surgical stapling device of claim 1, wherein the anvil retainer assembly includes a housing defining a lumen, the retainer member movably supported within the lumen of the housing and movable between retracted and advanced positions, wherein in the retracted position, the engagement member is retained in the non-pivoted position.

11. The surgical stapling device of claim 10, wherein the anvil retainer assembly includes a threaded drive screw, and the retainer member defines a threaded bore, the drive screw rotatable within the threaded bore to move the retainer member axially within the housing between the retracted and advanced positions.

12. The surgical stapling device of claim 1, wherein the anvil head is pivotally coupled to the anvil shaft.

13. A surgical stapling device comprising:
an elongate body portion having a proximal portion and a distal portion spaced from the proximal portion in a distal direction;
a shell assembly supported on the distal portion of the elongate body portion, the shell assembly including an annular cartridge positioned on a distal end of the shell assembly;
an anvil retainer assembly extending through the shell assembly and including a retainer member having a retainer body defining a first longitudinal axis that extends through the annular cartridge in the distal direction and an engagement member defining a second longitudinal axis, and a housing defining a lumen, the engagement member extending distally from the shell assembly in the distal direction and being pivotally supported on a distal portion of the retainer body, the engagement member movable between a first position in which the first and second longitudinal axes are aligned and a second position in which the first and second longitudinal axes are misaligned, the engagement member having a proximal portion received within the lumen when the engagement member is in the first position to retain the engagement member in the first position, the engagement member configured as a trocar having a tapered distal portion for piercing tissue; and
an anvil assembly including an anvil shaft and an anvil head, the anvil shaft releasably coupled to the engagement member.

14. The surgical stapling device of claim 13, wherein the retainer body includes a distal portion having a clevis and the engagement member includes a proximal extension, the clevis including spaced fingers, the proximal extension of the engagement member positioned between the spaced fingers of the clevis of the retainer body.

15. The surgical stapling device of claim 14, wherein the anvil retainer assembly includes a clevis pin, the proximal extension defining a slot and each of the spaced fingers of the clevis defining a through bore, the clevis pin positioned through the through bores of the spaced fingers and the slot of the proximal extension to pivotally secure the engagement member to the retainer body.

16. The surgical stapling device of claim 15, wherein the slot is elongated and the clevis pin is axially movable within the slot to facilitate axial movement of the engagement member in relation to the retainer body between advanced and retracted positions.

17. The surgical stapling device of claim 16, further including a biasing member positioned to urge the engagement member towards the retracted position.

18. The surgical stapling device of claim 13, wherein the anvil head is pivotally coupled to the anvil shaft.

19. An anvil retainer assembly comprising:
a retainer member having a retainer body defining a first longitudinal axis and an engagement member defining a second longitudinal axis, and a housing defining a third longitudinal axis and a lumen, the retainer body having a distal portion, the engagement member configured as a trocar having a tapered distal portion for piercing tissue, the engagement member extending distally from the lumen of the housing and being pivotally supported on the distal portion of the retainer body, the engagement member movable between a first position in which the first second, and third longitudinal axes are aligned and a second position in which the first and third longitudinal axes are misaligned with the second longitudinal axis, the engagement member having a proximal portion received within the lumen of the housing when the engagement member is in the first position to retain the engagement member in the first position.

20. The anvil retainer assembly of claim 19, wherein the retainer member is movably supported within the lumen of the housing for movement between retracted and advanced positions, the engagement member movable to the second position when the retainer member is in the advanced position and retained in the first position when the retainer member is in the retracted position.

\* \* \* \* \*